US007074803B2

(12) United States Patent
Litmanovitz et al.

(10) Patent No.: US 7,074,803 B2
(45) Date of Patent: Jul. 11, 2006

(54) OPIOID FORMULATIONS

(75) Inventors: Dana Litmanovitz, Sunnyvale, CA (US); Barbara J. F. Laidlaw, San Jose, CA (US)

(73) Assignee: Durect Corporation, Cupertino, CA (US)

( * ) Notice: Subject to any disclaimer, the term of this patent is extended or adjusted under 35 U.S.C. 154(b) by 336 days.

(21) Appl. No.: 10/220,525

(22) PCT Filed: Mar. 2, 2001

(86) PCT No.: PCT/US01/06955

§ 371 (c)(1),
(2), (4) Date: Jan. 23, 2003

(87) PCT Pub. No.: WO01/68140

PCT Pub. Date: Sep. 20, 2001

(65) Prior Publication Data

US 2003/0212106 A1    Nov. 13, 2003

(51) Int. Cl.
*A01N 43/42* (2006.01)
*C07D 211/36* (2006.01)
(52) U.S. Cl. ................ 514/282; 514/210; 546/242
(58) Field of Classification Search .............. 424/400; 546/242; 514/210, 282
See application file for complete search history.

(56) References Cited

U.S. PATENT DOCUMENTS

| 3,998,834 | A | 12/1976 | Janssen et al. |
| 4,588,580 | A | 5/1986 | Gale et al. |
| 4,769,372 | A | 9/1988 | Kreek |
| 5,202,128 | A | 4/1993 | Morella et al. |
| 5,378,474 | A | 1/1995 | Morella et al. |
| 5,910,301 | A | 6/1999 | Farr et al. |
| 6,113,937 | A * | 9/2000 | Vlaminck et al. ......... 424/422 |
| 6,703,483 | B1 * | 3/2004 | Schiller ...................... 530/330 |

FOREIGN PATENT DOCUMENTS

| EP | 0 267 617 A1 * | 5/1988 |
| WO | WO 90/07333 A1 | 7/1990 |
| WO | WO 92/02256 * | 2/1992 |
| WO | WO 95/31182 * | 11/1995 |
| WO | WO 97/49402 A1 | 12/1997 |
| WO | WO 00/54745 | 9/2000 |
| WO | WO 2004/047839 | 6/2004 |

OTHER PUBLICATIONS

Ramsay et al., (1995), "Immobilization of black bears (Ursus americanus) with orally administered carfentanil citrate", *Database Biosis Online!, Biosciences Information Service*, Philadelphia, PA US, database accession No. PREV 100598404995, abstract.

Ramsay et al., "Immobilization of black bears (*Ursus americanus*) with orally administered carfentanil citrate", Journal of Wildlife Diseases, (1995), 31(3): 391-393.
Anderson et al. (1998) "Alternate Routes of Opioid Administration in Palliative Care: Phamacologic and Clinical Concerns" *J. Pharm. Care Pain Symptom Control* 6:5-21.
Bruera et al. "Use of the Subcutaneous Route for the Administration of Narcotics in Patients with Cancer Pain" *Cancer* 62:407-11 (1988).
Clotz et al. "Clinical Uses of Fentanyl, Sufentanil, and Alfentanil" *Clin. Pharm.* 10:581-93 (1991).
Fudin et al. "Use of Continuous Ambulatory Infusions of Concentrated Subcutaneous (SQ) hydromorphone versus intravenous (IV) Morphine: Cost Implications for Palliative Care" Am J Hospice Pallitave Care 17:347-353 (2000).
Moulin et al. "Subcutaneous Narcotic Infusions for Cancer Pain: Treatment Outcome and Guidelines For Use" *Can. Med. Assoc. J.* 146:891-7(1992).
Paix et al. "Subcutaneous Fentanyl and Sufentanil Infusion Substitution For Morphine Intolerance In Cancer pain Management" *Pain* 63:263-9 (1995).
Physician's Desk Reference, Thomson Healthcare, Montvale, NJ, Ativan (2001) pp. 821. , 826, 828, 830, 831, 1193 and 1619.
Physician's Desk Reference, Thomson Healthcare, Montvale, NJ, Fentanyl (2001) pp. 826.
Physician's Desk Reference, Thomson Healthcare, Montvale, NJ, Meperidine (2001) pp. 828.
Physician's Desk Reference, Thomson Healthcare, Montvale, NJ, Morphine (2001) pp. 830.
Physician's Desk Reference, Thomson Healthcare, Montvale, NJ, Sulfentanil Citrate (2001) pp. 831.
Physician's Desk Reference, Thomson Healthcare, Montvale, NJ, Hydroxyzine Hydrochlroide (2001) pp. 1193.
Physician's Desk Reference, Thomson Healthcare, Montvale, NJ, Duramorph (2001) pp. 1195-1197.
Physician's Desk Reference, Thomson Healthcare, Montvale, NJ, Duragesic (2001) pp. 1573-1577.

(Continued)

*Primary Examiner*—Michael G. Hartley
(74) *Attorney, Agent, or Firm*—Durect Corporation; Thomas P. McCracken

(57) ABSTRACT

The present invention provides high-concentration formulations of opioids such as fentanyl or fentanyl congeners. The formulation of the invention comprises fentanyl or a fentanyl congener in concentrations significantly in excess of conventional formulations, e.g., on the order about 2-fold to about 10,000-fold greater than conventional formulations, e.g., currently commercially available formulations. These formulations are particularly useful for long-term delivery to a subject suffering from pain. The invention further provides drug delivery devices comprising the high-concentration opioid formulations, and further provides methods of alleviating pain in a subject, comprising administering the high-concentration formulations to a subject in need thereof.

2 Claims, No Drawings

OTHER PUBLICATIONS

Physician's Desk Reference, Thomson Healthcare, Montvale, NJ, Dilaudid (2001) pp. 1619-1623.

Scholz et al. ("Clinical Pharmacokinetics of Alfentanil, Fentanyl and Sufentanil" *Clin. Pharmacokinet.* 31:275-92 (1996).

Stephens "Intrathecal Narcotics for Labor Analgesia" *Am. Fam. Physician* 56:463-70 (1997).

Vercauteren et al. "Postoperative Intrathecal Patient-Controlled Analgesia With Bupivacaine, Sufentanil or a mixture of Both" *Anaesthesia* 53:1022-7 (1998).

Wagner et al. "Pharmacokinetics and Pharmacodynamics of Sedatives and Analgesics in the Treatment of Agitated Critically Ill Patients" Can Pharmakinet 33:426-53 (1997).

White "Clinical Uses of Intravenous Anesthetic and Analgesic Infusions" *Anesth. Analg.* 68:161-171 (1989).

Willens et al. Phamracodynamics, Pharmacokinetics, and Clinical Uses of Fentanyl, Sufentanil, and Alfentanil Heart Lung 22:239-52 (1993).

* cited by examiner

OPIOID FORMULATIONS

FIELD OF THE INVENTION

The invention relates to high-concentration formulations of opioids to alleviate pain.

BACKGROUND OF THE INVENTION

Opiates in various forms, including opium, heroine and morphine which derive from the opium poppy, have very powerful analgesic properties and have seen widespread use for anesthesia as well the treatment of pain, especially where the pain is very severe. In addition to these natural opiates, many synthetic opioids have since been synthesized including fentanyl and congeners of fentanyl such as sufentanil, alfentanil, lofentanil, carfentanil, remifentanil, etc., which are many times more potent than morphine.

At present, the dosage form with the most widespread use is still morphine administered orally, although opioids can also be delivered by intravenous infusion (see, e.g., Scholz et al. 1996 *Clin. Pharmacokinet.* 31:275–92; White 1989 *Anesth. Analg.* 68:161–71), oral administration, (see, e.g., U.S. Pat. Nos. 4,769,372; 5,202,128; and 5,378,474), epidural or intrathecal administration (see, e.g., Vercauteren et al. 1998 *Anaesthesia* 53:1022–7; Stephens 1997 *Am. Fam. Physician* 56:463–70), transdermal application (e.g., using a transdermal patch (see, e.g., U.S. Pat. No. 4,588,580)), or subcutaneous injection (see, e.g., Paix et al. 1995 *Pain* 63:263–9; Bruera et al. 1988 *Cancer* 62:407–11; Moulin et al. 1992 *Can. Med. Assoc. J.* 146:891–7). For a review, see, e.g., Clotz et al. 1991 *Clin. Pharm.* 10:581–93; and Anderson et al. 1998 *J. Pharm. Care Pain Symptom Control* 6:5–21.

Unfortunately, oral administration of morphine meets with several disadvantages. Many extremely ill patients can no longer take drugs orally for a variety of reasons, such as the inability to swallow or gastrointestinal obstruction. Furthermore, long-term oral administration often necessitates the ingestion of multiple pills or tablets many times a day, a dosing scheme commonly associated with poor compliance. For these and other reasons, parenteral administration of opioids can be a preferred alternative to oral administration.

However, parenteral administration of opioids meets with several challenges. Many patients, especially those with chronic-pain or diseases, require long-term treatment with opioids, e.g., for days, months, years and sometimes for the lifetime of the patient, and therefore require large quantities of drug to be administered over time. Also, many patients with severe pain require high doses of opioids to control pain, oftentimes with escalating requirements due to progression of the underlying disease state or development of tolerance to the opioid. Furthermore, in order to provide convenient, long-term or high-dosage pain treatment, opioids may need to be infused continuously and for long duration, usually by means of an infusion pump which can be an implantable or external pump. In order to provide acceptable convenience and mobility to patients, infusion pumps must be limited in size which in turn limits the volume of drug formulation that can be contained within. When opioids are administered for long durations using conventional formulations of opioids, the limited size of the drug reservoir of the pumps requires such pumps to be frequently refilled or exchanged which, besides being inconvenient, also requires the attention of a skilled health care worker and exposes the patient to possible infection.

Besides limitations imposed by pump size, the absorption capacity of the tissue into which the drug formulation is infused can limit the amount of volume of drug formulation that can be absorbed. For example, the absorptive capacity of the subcutaneous tissue is generally a maximum of 10 ml per hour (see e.g., Anderson et al., supra). Furthermore, infusions of large amounts of fluid into certain tissue can cause tissue edema which causes discomfort to the patient.

Currently available opioid formulations are too dilute to meet the needs of patients requiring long term treatment or large drug doses to control pain. For example, sufentanil citrate is currently available in an aqueous solution at a concentration of 50 µg/mL; morphine at 1 mg/mL; morphine sulfate at 20 mg/mL; fentanyl citrate at 20 µg/ml and alfentanil at 500 µg/mL. Simply adding more drug to conventional aqueous formulations is not a viable solution to creating more concentrated formulations as the opioid compound, especially those which are lipophilic such as fentanyl and its congeners, may precipitate out of solution which leads to, for example inconsistent delivery rates, reduced drug absorption, reduced tissue response and clogging of the drug delivery device or other points along the infusion pathway.

For the foregoing discussion, it is evident that there is a need in the art for more concentrated opioid formulations that permit convenient long-term or high dose delivery yet is stable over time and safe for parenteral use. The present invention addresses this need, and provides related advantages as well.

SUMMARY OF THE INVENTION

The present invention provides opioid formulations suitable for long-term delivery to a subject. The formulation of the invention comprises fentanyl or a fentanyl congener, and a solvent in which the fentanyl or fentanyl congener can be provided in concentrations significantly in excess of conventional formulations, e.g., on the order about 2-fold to about 10,000-fold greater than conventional formulations, e.g., currently commercially available formulations. In the present invention, concentrated opioid formulations useful for parenteral delivery are created by solubilizing in non-aqueous solutions extremely potent opioid compounds, e.g., fentanyl and its congeners, which are hundreds to thousands of times more potent than morphine. The formulations of the invention are especially useful for high-dose delivery, or long-term delivery, e.g., several hours, weeks, months, or even years. Long-term delivery can be achieved using various external or implanted devices.

The invention further provides a sustained release dosage form comprising a formulation of the invention. The dosage form can be an external, partially implanted, or implanted device (e.g., biodegradable implants or pumps), which can be based on, for example, drug diffusion systems, electrochemical systems, electromechanical systems, osmotic pumps, electrodiffusion systems, electroosmosis systems, vapor pressure pumps, electrolytic pumps, effervescent pumps, piezoelectric pumps, erosion-based systems, diffusive systems and the like.

The invention further provides methods of treating pain in a subject, comprising delivering from a drug delivery device a fentanyl or fentanyl congener formulation of the invention to a site in the body of the subject. Delivery of the formulation is generally continuous, and can be for a pre-selected administration period ranging from several hours, one to several weeks, one to several months, up to one or more years.

Pain amenable to alleviation includes all types of acute or chronic pain, e.g., cancer pain, chronic inflammatory disease pain, neuropathic pain, post-operative pain, iatrogenic pain, complex regional pain syndrome, failed-back pain, soft tissue pain, joint pain, bone pain, central pain, injury pain, arthritic pain, hereditary disease, infectious disease, headache, causalgia, hyperesthesia, sympathetic dystrophy, phantom limb syndrome, and denervation.

A primary advantage of the present invention is that very potent and concentrated opioid formulations can be achieved by solubilizing very potent opioids in a small volume of solvent. This makes it possible to provide therapeutic amounts of drug to a subject in the case where the delivery device is relatively small (e.g., an implantable system), where delivery is required for a relatively long duration, or where high effective doses of drug are required to achieve the desired therapeutic effect.

Thus, it is possible to deliver a consistent amount of drug over an extended period of time without the need to refill or replace the delivery device, thereby reducing risk of infection and tissue damage, increasing patient compliance, and achieving consistent, accurate dosing.

A primary advantage of the formulations of the invention is that high concentrations of fentanyl or fentanyl congener are achieved without substantial precipitation of the drug.

Another important advantage of the formulations of the present invention is that therapeutic amounts of drug (even high doses) can be delivered to internal tissues of the body at a low volume rate. For certain body tissues, e.g., subcutaneous space, low volume delivery can make the delivered formulation more amenable to absorption by the local tissue, and further minimizes local tissue disturbance, trauma, or edema.

A further advantage of the formulations of the invention is that precipitation of the fentanyl/fentanyl congener does not occur when the formulation comes into contact with aqueous environment, such as body fluids. Precipitation of drug is clearly undesirable, since it could lead to local toxic effects, or clogging of the delivery orifice or elsewhere along the delivery route, resulting in uncontrolled delivery or complete stoppage of delivery, which would adversely affect consistency and accuracy of dosing and therefore patient safety. The formulations of the invention avoid these potential problems.

These and other objects, advantages, and features of the invention will become apparent to those persons skilled in the art upon reading the details of the invention as more fully described below.

DETAILED DESCRIPTION OF THE INVENTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a formulation" includes a plurality of such formulations and reference to "the fentanyl congener" includes reference to one or more fentanyl congeners and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The terms "drug" and "therapeutic agent," used interchangeably herein, are generally meant to refer to fentanyl or a fentanyl congener (e.g., sufentanil, alfentanil, lofentanil, carfentanil, remifentanil, trefentanil, and mirfentanil), as well as formulations comprising one or more of these compounds. Use of "drug" or the phrase "fentanyl or fentanyl congener" is not meant to be limiting to use of, or formulations comprising, only one of these selected opioid compounds. Furthermore, reference to fentanyl alone or to a selected fentanyl congener alone, e.g., reference to "sufentanil," is understood to be only exemplary of the drugs suitable for use in formulations according to the invention, and is not meant to be limiting in any way.

The term "subject" is meant any subject, generally a mammal (e.g., human, canine, feline, equine, bovine, etc.), in which management of pain is desired.

The term "therapeutically effective amount" is meant an amount of a therapeutic agent, or a rate of delivery of a therapeutic agent, effective to facilitate a desired therapeutic effect. The precise desired therapeutic effect (e.g., the degree of pain relief, and source of the pain relieved, etc.) will vary according to the condition to be treated, the formulation to be administered, and a variety of other factors that are appreciated by those of ordinary skill in the art. In general, the method of the invention involves the suppression or mitigation of pain in a subject suffering from pain that may be associated with any of a variety of identifiable or unidentifiable etiologies.

The term "pain management" is used here to generally describe regression, suppression, or mitigation of pain, including acute and chronic pain, so as to make the subject more comfortable as determined by subjective criteria, objective criteria, or both. In general, pain is assessed subjectively by patient report, with the health professional taking into consideration the patient's age, cultural background, environment, and other psychologic background factors known to alter a person's subjective reaction to pain.

"Delivery site" as used herein is meant to refer to an area of the body to which drug is delivered. Such delivery sites include, but are not necessarily limited to, intravenous, intraspinal (e.g., epidural, subdural, or intrathecal), intracerebral, transdermal, or subcutaneous sites of delivery and the like. Subcutaneous delivery sites are of particular interest in the present application. Exemplary subcutaneous delivery sites include external subcutaneous sites (e.g., under the skin of the arm, shoulder, neck, back, or leg) and internal subcutaneous sites within a body cavity (e.g., within the mouth).

"Drug delivery device" as used herein is meant to refer to any device suitable for delivering the formulations for pain management according to the invention. "Drug delivery device" thus encompasses, but is not necessarily limited to, external or implanted dosage forms (e.g., biodegradable implants or pumps) with any mechanism of action, which dosage forms can be based on, for example, diffusive, erodible, or convective systems, e.g., osmotic pumps, biodegradable implants, electrodiffusion systems, electroosmosis systems, electrochemical systems, vapor pressure pumps, electrolytic pumps, effervescent pumps piezoelectric pumps, erosion-based systems, electromechanical systems, diffusive systems, etc.

"Patterned" or "temporal" as used in the context of drug delivery is meant delivery of drug in a pattern, generally a substantially regular pattern, over a pre-selected period of time (e.g., other than a period associated with, for example a bolus injection). "Patterned" or "temporal" drug delivery is meant to encompass delivery of drug at an increasing, decreasing, substantially constant, or pulsatile, rate or range of rates (e.g., amount of drug per unit time, or volume of drug formulation for a unit time), and further encompasses delivery that is continuous or substantially continuous, or chronic.

The term "controlled drug release device" or "controlled release dosage form" is meant to encompass any device wherein the release rate (e.g., rate of timing of release) of a drug or other desired substance contained therein is controlled by the device or dosage form itself and substantially not the environment of use, and that can be adapted for use in the invention, e.g., a dosage form that provides for controlled release of drug and at a rate that is suitable to accomplish delivery of a therapeutically effective amount of fentanyl or a fentanyl congener according to the invention to a site within the body. The terms "device" and "dosage form" are generally used interchangeably herein.

The term "sustained release dosage form" is meant to refer to a drug dosage form that is adapted for release of a drug formulation (e.g., an opiod) over a pre-selected period of time rather than at one time as in a bolus administration (e.g., by injection or oral administration). Sustained release dosage forms can include dosage forms capable of controlled release or patterned release of a drug.

"Treatment" as in "treatment of pain" is used herein to encompass both a decrease in pain severity and/or intensity to provide partial or complete relief of pain and/or pain symptoms. The effect may be prophylactic in terms of completely or partially preventing or reducing the severity of pain.

Overview of the Invention

The present invention is based on the finding that opioid such as fentanyl and its congeners can be formulated at higher concentrations than were previously attained. Controlled delivery of fentanyl or a fentanyl congener, e.g., sufentanil, over a prolonged period of time, e.g. weeks or months, from a conveniently sized delivery system, e.g., an implantable pump, that requires highly concentrated formulations. However, fentanyl and its congeners have very low solubility in aqueous vehicles typically used in formulations of these compounds. An aqueous formulation would thus not provide sufficient drug concentration to meet the desired dosing requirements for a system with a small drug reservoir, e.g., an implantable system, without the need for frequent re-filling of the drug reservoir or providing a new implant. In addition, the highly concentrated formulation of the fentanyl or fentanyl congener must be stable (e.g., at body temperatures in the case of an implanted system) and must maintain the solubility of the drug as it is delivered to the aqueous environment of the body in order to avoid precipitation and interference of the function of the delivery system (e.g., by blockage of the delivery orifice or elsewhere along the delivery pathway in a pump system).

The present invention provides formulations of fentanyl congeners which are characterized in that: (1) they have a fentanyl or fentanyl congener concentration of about 2 to about 10,000 times or greater than that of currently commercially available formulations; (2) the fentanyl or fentanyl congener does not precipitate out when the formulation comes into contact with an aqueous environment, e.g., in the body of the subject being treated; and (3) have good stability, even at body temperatures. For example, a formulation of sufentanil in accordance with the present invention are advantageous over current commercially available sufentanil injection formulation, which contain only about 50 μg/mL sufentanil as the citrate salt in aqueous solution.

Formulations Comprising High Concentrations of Fentanyl or a Fentanyl Congener

The invention provides a formulation, particularly a pharmaceutical formulation, comprising fentanyl or a fentanyl congener.

The fentanyl or fentanyl congener is present in the formulation in a concentration substantially higher than conventional formulations, e.g., current commercially available formulations. By "substantially higher," it is intended that the fentanyl or fentanyl congener is present in the formulation in a concentration of at least about 2, at least about 5, at least about 10, at least about 20, at least about 50, at least about 100, at least about 250, at least about 500, at least about 1000, at least about 1500, at least about 2000, at least about 2500, at least about 3000, at least about 3500, at least about 4000, at least about 5000, at least about 6000, at least about 7000, at least about 8000, at least about 9000, at least about 10,000 times, or greater, than the solubility of fentanyl or fentanyl congener in aqueous solution.

Formulations of the invention comprise fentanyl or a fentanyl congener in a concentration of at least about 0.1 mg/mL, 0.5 mg/mL, 1 mg/mL, 10 mg/mL, 25 mg/mL, 50 mg/mL, 75 mg/mL, 100 mg/mL, 150 mg/mL, 200 mg/mL, 225 mg/mL, 250 mg/mL, 300 mg/mL, 350 mg/mL, 400 mg/mL, 450 mg/mL, 500 mg/mL, or greater. Formulations of the invention comprising fentanyl or fentanyl congener are in solution, e.g., are dissolved in a liquid.

Pharmaceutical grade organic or inorganic carriers and/or diluents suitable for systemic delivery can be included in the formulation suitable for delivery according to the invention. Such physiologically acceptable carriers are well known in the art. Exemplary liquid carriers for use in accordance with the present invention can be sterile non-aqueous or aqueous solutions which contain no materials other than the active ingredient. In general, hydrophobic solvents are generally preferred due to the lipophilicity of fentanyl and fentanyl congeners. The formulations can optionally further comprise a buffer such as sodium phosphate at physiological pH value, physiological saline or both (e.g., phosphate-buffered saline). Suitable aqueous carriers may optionally further comprise more than one buffer salt, as well as other salts (such as sodium and potassium chlorides) and/or other solutes.

In general, fentanyl or fentanyl congeners are present in the formulations of the present invention as a fentanyl base or fentanyl congener base, although a formulation of the invention may comprise fentanyl or a fentanyl congener in a form other than a base form, as discussed in more detail below.

In some embodiments, a formulation comprises fentanyl or a fentanyl congener and a low molecular weight (e.g., MW less than about 300 g/mol) alcohol. In these embodiments, the fentanyl or fentanyl congener is present in the formulation in a concentration of from about 0.5 mg/mL to about 500 mg/mL, from about 1 mg/mL to about 450 mg/mL, from about 50 mg/mL to about 400 mg/mL, from about 75 mg/mL to about 300 mg/mL, or from about 100 mg/mL to about 250 mg/mL. Suitable low molecular weight alcohols include those which are pharmaceutically acceptable, and which preferably comprise an aromatic moiety, and which are relatively immiscible in water (e.g., less than about 5, less than about 4, less than about 3, less than about 2, less than about 1 gram can dissolve in 25 ml $H_2O$), including, but not limited to, benzyl alcohol, and derivatives thereof. Small amounts of other pharmaceutically acceptable substances such as other pharmaceutically acceptable alcohols, e.g., ethanol, or water, may also be present, and, if present, are present in an amount of less than about 10%, less than about 5%, or less than about 1%. In a particular embodiment, the formulation comprises fentanyl or fentanyl congener in 100% benzyl alcohol.

In some embodiments, a formulation comprises fentanyl or a fentanyl congener, and a nonionic surfactant, in an alcohol ester, e.g., an ester of a low molecular weight alcohol as described above. In these embodiments, the fentanyl or fentanyl congener is present in the formulation in a concentration of from about 0.5 mg/mL to about 500 mg/mL, from about 1 mg/mL to about 450 mg/mL, from about 50 mg/mL to about 300 mg/mL, from about 75 mg/mL to about 275 mg/mL, or from about 100 mg/mL to about 250 mg/mL. Suitable alcohol esters include those which are pharmaceutically acceptable, which preferably comprise an aromatic moiety, and which are insoluble in water, including, but not limited to, benzyl benzoate, and derivatives thereof. Small amounts of pharmaceutically acceptable substances such as pharmaceutically acceptable alcohols or other pharmaceutically acceptable alcohol esters, or water, may also be present, and, if present, are present in an amount of less than about 10%, less than about 5%, or less than about 1%. In a particular embodiment, the alcohol ester is 100% benzyl benzoate.

Suitable nonionic surfactants include those which are pharmaceutically acceptable, including but not limited to, polysorbate, e.g., polysorbate 20, polysorbate 40, polysorbate 60; sorbitan trioleate; polyoxyethylene polyoxypropyleneglycol, e.g., polyoxyethylene(160)glycol, and polyoxypropylene(30)glycol. Other nonionic surfactants which are suitable for use in the formulations of the present invention include nonionic surfactants of the fatty acid polyhydroxy alcohol ester type such as sorbitan monolaurate, monooleate, monostearate or monopalmitate, sorbitan tristearate or trioleate, adducts of polyoxyethylene and fatty acid polyhydroxy alcohol esters such as polyoxyethylene sorbitan monolaurate, monooleate, monostearate, monopalmitate, tristearate or trioleate, polyethylene glycol fatty acid esters such as polyoxyethyl stearate, polyethylene glycol 400 stearate, polyethylene glycol 2000 stearate, in particular ethylene oxide-propylene oxide block copolymers of the Pluronics™ (Wyandotte) or Synperonic™ (ICI). In particular embodiments, the nonionic surfactant is polysorbate 20, polysorbate 40, polysorbate 60, or sorbitan trioleate, or mixtures of one or more of the foregoing.

In general, a nonionic surfactant is present in the formulation in a concentration of from about 50 mg/mL to about 200 mg/mL, from about 75 mg/mL to about 175 mg/mL, or from about 100 mg/mL to about 150 mg/mL. In a particular embodiment, the nonionic surfactant is present in the formulation at 100 mg/mL.

The formulations of the present invention are characterized in that the fentanyl or fentanyl congener is present in a high concentration, as described above. The fentanyl or fentanyl congener is soluble in the formulation, i.e., little or no fentanyl or fentanyl congener precipitates are present, and further, little or no fentanyl or fentanyl congener precipitates when the formulation comes in contact with an aqueous environment such as a body fluid. Precipitates of fentanyl or fentanyl congeners, when present at all, are present in the formulation at less than about 10%, less than about 7.5%, less than about 5%, less than about 2.5%, less than about 1%, or less than about 0.1% by weight of the total fentanyl or fentanyl congener present in the formulation. Whether precipitates have formed can be determined using any method known in the art, including, but not limited to, visual inspection with the unaided eye, or under low (e.g., 10× or 25×) magnification.

Exemplary additional active ingredients that can be present in the formulations useful with the invention can include an opioid antagonist (e.g., to further decrease the possibility of addiction or dependence, see, e.g., an exemplary osmotic dosage formulation comprising an opioid agonist and an opioid antagonist is described in U.S. Pat. No. 5,866,164.

Fentanyl and Fentanyl Congeners

Fentanyl, congeners of fentanyl, and specific derivatives or analogs of fentanyl or fentanyl congeners (e.g., other derivatives, particularly 4-anilidopiperidine derivatives, of morphine) are contemplated for delivery according to the invention, although variations within the scope of the invention will be readily apparent to the ordinarily skilled artisan upon reading the disclosure provided herein. Exemplary fentanyl congeners include, but are not necessarily limited to sufentanil, alfentanil, lofenatnil, carfentanil, remifentanil, trefentanil, and mirfentanil.

The specific fentanyl congener used can vary with a variety of factors, including the therapeutic effect desired to be achieved, the patient's tolerance and/or previous exposure to opioids, etc. The relative potency of fentanyl or the fentanyl congener may also be considered in selection of the drug to be delivered. For example, the rank order of potency of fentanyl and selected fentanyl congeners relative to morphine is as follows: morphine<alfentanil<fentanyl<sufentanil<lofentanil <carfentanil. Fentanyl is 292 times, sufentanil, 4,521 times, lofentanil 5,440 times, and carfentanil 9,441 times more potent than morphine. For a review of the pharmacokinetics of sufentanil, fentanyl, and other fentanyl congeners, see, e.g., Meert (1996) *Pharm. World Sci.* 18:1–15; Scholz et al. 1996 *Clin. Pharmacokinet.* 31:275–92.

Methods for manufacture of fentanyl, sufentanil and other fentanyl congeners are well known in the art, see, e.g., sufentanil (e.g., U.S. Pat. No. 3,998,834; chemical name: ((N-[4-(methyoxymethyl)-1-[2-(2-thienyl)ethyl]-4-piperidinyl]-N-phenylpropanamide 2-hydroxy-1,2,3,-propanetricarboxylate (1:1); $C_{22}H_{30}N_2O_2S$), fentanyl (e.g., U.S. Pat. No. 3,141,823; chemical name: N-phenyl-N-[1-(2-phenylethyl)-4-piperidinyl]propanamide), alfentanil (e.g., U.S. Pat. No.

4,167,574; chemical name: N-[1-[2-(4-ethyl-4,5-dihydro-5-oxo-1H-tetrazol-1-yl)ethyl]-4-(methoxymethyl)-4-piperidinyl]-N-phenylpropanamide ($C_{21}H_{32}N_6O_3$)), lofenatnil (e.g., U.S. Pat. No. 3,998,834; chemical name: 3-methyl-4-[(1-oxopropyl)phenylamino]-1-(2-phenylethyl)-4-piperidinecarboxylic acid methyl ester), carfentanil (chemical name: methyl-4-[(1-oxopropyl)phenylamino]-1-(2-phenylethyl)-4-piperidinecarboxylate ($C_{24}H_{30}N_2O_3$)), remifentanil (chemical name: 3-[4-methoxycarbonyl-4-[(1-oxopropyl) phenylamino]1-piperidine]propanoic acid), trefentanil (chemical name: N-(1-(2-(4-ethyl-4,5-dihydro-5-oxo-1H-tetrazol-1-yl)ethyl)-4phenyl-4-piperidinyl)-N-(2-fluorophenyl)-propanamide, and mirfentanil (chemical name: [N-(2-pyrazinyl)-N-(1-phenethyl-4-piperidinyl)-2-furamide).

Fentanyl and fentanyl congeners are discussed in detail in, for example, Goodman and Gilman's The Pharmacological Basis of Therapeutics, Chapter 23, "Opioid Analgesics and Antagonists", pp. 521–555 ($9^{th}$ Ed. 1996); Baly et al. 1991 Med Res. Rev. 11:403–36 (evolution of the 4-anilidopiperidine opioids); and Feldman et al. 1991 J. Med. Chem. 34:2202–8 (design, synthesis, and pharmacological evaluation of opioid analgesics). For additional information on fentanyl and fentanyl congeners, see, e.g., Scholz et al. 1996 Clin. Pharmacokinet. 31:275–92 (clinical pharmacokinetics of alfentanil, fentanyl, and sufentanil); Meert 1996 Pharmacy World Sci. 18:1–15 (describing pharmacotherapy of morphine, fentanyl, and fentanyl congeners); Lemmens et al. 1995 Anesth. Analg. 80:1206–11 (pharmacokinetics of mirfentanil); Minto et al., 1997 Int. Anesthesiol. Clin. 35:49–65 (review of recently developed opioid analgesics); James 1994 Expert Opin. Invest. Drugs 3:331–40 (discussion of remifentanil); Rosow 1993 Anesthesiology 79:875–6 (discussion of remifentanil); Glass 1995 Eur. J. Anaesthesiol. Suppl. 10:73–4. (pharmacology of remifentanil); and Lemmens et al. 1994 Clin. Pharmacol. Ther. 56:261–71 (pharmacokinetics of trefentanil)

Fentanyl or a fentanyl congener can be provided in the formulation as the opioid base and/or the opioid pharmaceutically acceptable salt, but is preferably provided in the formulation as the opioid base. The pharmaceutically acceptable salt embraces the inorganic and the organic salt. Representative salts include a member selected from the group consisting of hydrobromide, hydrochloride, mucate, citrate, succinate, n-oxide, sulfate, malonate, acetate, phosphate dibasic, phosphate monobasic, acetate trihydrate, bi(heptafluorobutyrate), maleate, bi(methylcarbamate), bi(pentafluoropropionate), mesylate, bi(pyridine-3-carboxylate), bi(trifluoroacetate), bitartrate, chlorhydrate, fumarate and sulfate pentahydrate. Where the drug formulation comprises sufentanil, use of the sufentanil base is specifically contemplated for use.

Dosage Forms Useful in the Methods of the Invention

Any of a variety of dosage forms can be used in conjunction with a formulation of the present invention. Delivery methods and dosage forms suitable for use with the formulations of the present invention can take advantage of any of a variety of drug release mechanisms.

In general, the dosage forms suitable for use in the invention are adapted for retaining a quantity of drug formulation (e.g., contained in a drug reservoir or solubilized, suspended or integrated into a vehicle, substrate or matrix such as a polymer, binding solid, etc.) sufficient for treatment for a pre-selected period. In general the dosage forms for use with the present invention are adapted for sustained release of the formulation. Exemplary dosage forms include drug delivery devices (e.g., drug pumps), bioerodable implants, sustained release injectables (e.g., injectable high viscous formulations, gels including hydrogels such as collagen hydrogels), microparticulate suspensions, microsphere suspensions, liposome formulations, micelle formulations, oil suspensions (including emulsions), and encapsulated particulate suspensions. Drug delivery dosage forms that may be suitable for use with the present invention are described in Encyclopedia of Controlled Drug Delivery (1999), Edith Mathiowitz (Ed.), John Wiley & Sons, Inc. The dosage form can be selected from, for example, any of a variety of conventional drug release devices that are conventionally used as an external element (e.g., an external pump) or implanted element of a drug delivery system.

In some embodiments, the dosage form (also referred to herein as a delivery device) is one that is adapted for delivery of fentanyl or fentanyl congener over extended periods of time. Such delivery devices may be adapted for administration of fentanyl or fentanyl congener for several hours (e.g. 2 hours, 12 hours, or 24 hours to 48 hours or more), to several days (e.g., 2 to 5 days or more, from about 100 days or more), to several months or years. In some of these embodiments, the device is adapted for delivery for a period ranging from about 1 month to about 12 months or more. The drug delivery device may be one that is adapted to administer fentanyl or fentanyl congener to an individual for a period of, e.g., from about 2 hours to about 72 hours, from about 4 hours to about 36 hours, from about 12 hours to about 24 hours; from about 2 days to about 30 days, from about 5 days to about 20 days, from about 7 days to about 100 days or more, from about 10 days to about 50 days; from about 1 week to about 4 weeks; from about 1 month to about 24 months or more, from about 2 months to about 12 months, from about 3 months to about 9 months; or other ranges of time, including incremental ranges, within these ranges, as needed.

Release of drug from the dosage form, particularly controlled release of drug, can be accomplished in any of a variety of ways according to methods well known in the art, e.g., by solubilization or suspension of drug in a vehicle or incorporation of drug into a polymer that provides for substantially controlled diffusion of drug from within the polymer, incorporation of drug in a biodegradable polymer, providing for delivery of drug from an osmotically-driven device, etc. Where the drug delivery device comprises a drug delivery catheter, drug can be delivered through the drug delivery catheter to the delivery site as a result of capillary action, as a result of pressure generated from the drug device, by diffusion, by electrodiffusion or by electroosmosis through the device and/or the catheter.

In general, the dosage form is adapted to carry the drug formulation in such quantities and concentration as therapeutically required for treatment over the pre-selected period, and must provide sufficient protection to the formulation from degradation by body processes for the duration of treatment. For example, the dosage form can be surrounded by an exterior made of a material that has properties to protect against degradation from metabolic processes and the risk of, e.g., leakage, cracking, breakage, or distortion. This can prevent expelling of the dosage form contents in an uncontrolled manner under stresses it would be subjected to during use, e.g., due to physical forces exerted upon the drug release device as a result of movement by the subject or for example, in convective drug delivery devices, physical forces associated with pressure generated within the reservoir. The drug reservoir or other means for holding or containing the drug must also be of such material as to avoid unintended reactions with the active agent formulation, and is preferably biocompatible (e.g., where the dosage form is implanted, it is substantially non-reactive with respect to a subject's body or body fluids).

Suitable materials for the reservoir or drug holding means for use in the delivery devices of the invention are well known in the art. For example, the reservoir material may comprise a non-reactive polymer or a biocompatible metal or alloy. Suitable polymers include, but are not necessarily limited to, acrylonitrile polymers such as acrylonitrile-butadiene-styrene polymer, and the like; halogenated polymers such as polytetrafluoroethylene, polyurethane, polychlorotrifluoroethylene, copolymer tetrafluoroethylene and hexafluoropropylene; polyethylene vinylacetate (EVA), polyimide; polysulfone; polycarbonate; polyethylene; polypropylene; polyvinylchloride-acrylic copolymer; polycarbonate-acrylonitrile-butadiene-styrene; polystyrene; cellulosic polymers; and the like. Further exemplary polymers are described in The Handbook of Common Polymers, Scott and Roff, CRC Press, Cleveland Rubber Co., Cleveland, Ohio.

Metallic materials suitable for use in the reservoir of the drug delivery devices include stainless steel, titanium, platinum, tantalum, gold and their alloys; gold-plated ferrous alloys; platinum-plated titanium, stainless steel, tantalum, gold and their alloys as well as other ferrous alloys; cobalt-chromium alloys; and titanium nitride-coated stainless steel, titanium, platinum, tantalum, gold, and their alloys.

Exemplary materials for use in polymeric matrices include, but are not necessarily limited to, biocompatible polymers, including biostable polymers and biodegradable polymers. Exemplary biostable polymers include, but are not necessarily limited to silicone, polyurethane, polyether urethane, polyether urethane urea, polyamide, polyacetal, polyester, poly ethylene-chlorotrifluoroethylene, polytetrafluoroethylene (PTFE or "Teflon™"), styrene butadiene rubber, polyethylene, polypropylene, polyphenylene oxide-polystyrene, poly-a-chloro-p-xylene, polymethylpentene, polysulfone and other related biostable polymers. Exemplary biodegradable polymers include, but are not necessarily limited to, polyanhydrides, cyclodestrans, polylactic-glycolic acid, polyorthoesters, n-vinyl alcohol, polyethylene oxide/polyethylene terephthalate, polyglycolic acid, polylactic acid, sucrose acetate isobutyrate, and other related bioabsorbable polymers.

Where the drug formulation is stored in a reservoir comprising metal or a metal alloy, particularly titanium or a titanium alloy having greater than 60%, often greater than 85% titanium is preferred for the most size-critical applications, for high payload capability and for long duration applications and for those applications where the formulation is sensitive to body chemistry at the implantation site or where the body is sensitive to the formulation. Most preferably, the drug delivery devices are designed for storage with drug at room temperature or higher.

Drug release devices suitable for use in the invention may be based on any of a variety of modes of operation. For example, the drug release device can be based upon a diffusive system, a convective system, or an erodible system (e.g., an erosion-based system). For example, the drug release device can be an osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump, can also be suitable for use with the present invention. Examples of such devices include those described in, for example, U.S. Pat. Nos. 4,692,147; 4,360,019; 4,487,603; 4,360,019; 4,725,852, and the like. In general, the present methods of drug delivery can be accomplished using any of a variety of refillable, non-exchangeable pump systems. Pumps and other convective systems are generally preferred due to their generally more consistent, controlled release over time. Osmotic pumps are particularly preferred due to their combined advantages of more consistent controlled release and relatively small size. Exemplary osmotically-driven devices suitable for use in the invention include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; 5,985,305; and the like.

In one embodiment, the drug release device is a controlled drug release device in the form of an osmotically-driven device. Preferred osmotically-driven drug release systems are those that can provide for release of agent in a range of rates of from about 0.01 mg/hr to about 1000 mg/hr, and which can be delivered at a volume rate range of, for example, from about 0.001 ml/day to about 100 ml/day (i.e., from about 0.0004 ml/hr to about 4 ml/hr), from about 0.04 ml/day to about 10 ml/day, from about 0.2 ml/day to about 5 ml/day, from about 0.5 ml/day to about 1 ml/day In general, in the present invention, the drug release system is selected to provide for delivery of a bisphosphonate at a rate of from about 0.001 ml/day (1 ml/day) to at least about 500 ml/day or about 1 ml/day (i.e., from about 0.04 ml/hr to about 21 ml/hr to about 42 ml/hr), from about 2 ml/day to about 250 ml/day to 500 ml/day, from about 4 ml/day to about 100 ml/day, from about 5 ml/day to about 50 ml/day to 250 ml/day.

In an embodiment, the sustained release dosage form is a depot-type injectable, see e.g., U.S. Pat. Nos. 6,183,781; 6,174,547; 6,156,331; 6,143,314; 6,130,200; 6,120,789; 6,051,558; 5,989,463; 5,968,542; 5,912,015; 5,747,058; 5,702,716; 5,654,008; and 5,650,173.

In one embodiment of particular interest, the volume/time delivery rate is substantially constant (e.g., delivery is generally at a rate ± about 5% to 10% of the cited volume over the cited time period). In one embodiment, the drug release device is a continuous drug release device in the form of an osmotically-driven device. Preferred osmotically-driven drug release systems are those that can provide for release of drug in a range of rates of from about 0.1 mg/hr to about 1000 mg/hr, and which can be delivered at a volume rate of from about 0.25 ml/day to about 100 ml/day (i.e., from about 0.0004 ml/hr to about 4 ml/hr), from about 0.04 ml/day to about 10 ml/day, and can be from about 0.2 ml/day to about 5 ml/day, or from about 0.5 ml/day to about 1 ml/day. In one embodiment, the volume/time delivery rate is substantially constant (e.g., delivery is generally at a rate ± about 5% to 10% of the cited volume over the cited time period).

The invention features methods for management of pain by delivery of a formulation of the invention. In one embodiment, the drug formulation of the invention is delivered in a substantially continuous fashion. While the formulations of the invention can be delivered to any of a variety of delivery sites, the formulations can find particular use in delivery of fentanyl or a fentanyl congener (particularly sufentanil) to a subcutaneous site. Methods of subcutaneous delivery fentanyl or a fentanyl congener (particularly sufentanil) are described in the U.S. regular utility application entitled "Devices and Methods for Pain Management," U.S. application Ser. No. 09/522,535 filed on Aug. 3, 2000, which application is specifically incorporated herein by reference.

Methods of Alleviating Pain in a Subject Using a Formulation of the Invention

Although the formulations of the present invention can be used for a variety of therapeutic purposes for which opioids are suitable, the formulations of the invention are particularly useful for alleviating pain in a subject suffering from pain, such methods comprising administering to a subject suffering from pain a formulation of the present invention. In particular embodiments, the formulation is administered using a drug delivery device suitable for long-term delivery, e.g., a drug delivery device as described above. In general, the methods comprise delivering from a drug delivery device a formulation comprising fentanyl or fentanyl congener in an amount effective to alleviate pain in the subject.

Subjects suffering from or susceptible to pain can receive alleviation of pain according to the method of the invention for any desired period of time. In general, administration of fentanyl or fentanyl congener according to the invention can be sustained for several hours (e.g., 2 hours, 12 hours, or 24 hours to 48 hours or more), to several days (e.g., 2 to 5 days or more), to several months or years. Typically, delivery can be continued for a period ranging from about 1 month to about 12 months or more. The fentanyl or fentanyl congener may be administered to an individual for a period of, for example, from about 2 hours to about 72 hours, from about 4 hours to about 36 hours, from about 12 hours to about 24 hours, from about 2 days to about 30 days, from about 5 days to about 20 days, from about 7 days to about 100 days or more, from about 10 days to about 50 days, from about 1 week to about 4 weeks, from about 1 month to about 24 months, from about 2 months to about 12 months, or from about 3 months to about 9 months, or other ranges or time, including incremental ranges with these ranges, as needed. This extended period of opioid delivery is made possible by the high concentration of opioids present in the formulations of the invention. In particular embodiments, the fentanyl or fentanyl congener is delivered to the subject without the need for re-accessing the device and/or without the need for re-filling the device. In these embodiments, high-concentration formulations of fentanyl or fentanyl congener are of particular interest.

Preferably, delivery of fentanyl or fentanyl congener is substantially continuous, e.g., substantially uninterrupted for a pre-selected period of drug delivery, and more preferably at a substantially constant, pre-selected rate or range of rates (e.g., amount of drug per unit time, or volume of drug formulation for a unit time). The drug is preferably delivered at a volume rate of from about 0.01 μl/day to about 2 ml/day, preferably about 0.04 μl/day to about 1 ml/day, generally about 0.2 μl/day to about 0.5 ml/day, typically from about 2.0 μl/day to about 0.25 ml/day.

In one embodiment, a drug delivery device provides for substantially continuous delivery of drug at a preselected rate. For example, for subcutaneous delivery of sufentanil, the drug can be delivered at a rate of from about 0.1 μg/hr to about 200 μg/hr, from about 0.25 μg/hr to about 100 μg/hour, usually between about 3 μg/hr to about 85 μg/hr, and typically between about 5 μg/hr to about 100 μg/hr. In a specific exemplary embodiment, sufentanil is delivered at a rate of from about 0.01 μg/hour, about 0.1 μg/hour, about 0.25 μg/hour, or about 1 μg/hour, generally up to about 200 μg/hour. Appropriate amounts of fentanyl or fentanyl congener can be readily determined by the ordinarily skilled artisan based upon, for example, the relative potency of these drugs. The actual dose of drug delivered will vary with a variety of factors such as the potency and other properties of the selected drug used (e.g., lipophilicity, etc.).

Substantially continuous delivery of fentanyl or fentanyl congener (e.g., by infusion, diffusion, etc.) according to the invention can be accomplished using, for example, a drug delivery device in the form of an external or implantable pump. Use of such drug delivery devices provides at least the following additional advantages: (1) the therapeutic analgesic effect of the drug(s) is essentially continuous; (2) drug is delivered to the subject in a smooth and consistent fashion (e.g., the bolus effect is substantially avoided both at the initiation of therapy and throughout the pre-selected period of therapy); (3) the potential for misuse or abuse of the opioid is substantially diminished (e.g., the patient does not have ready access to a surplus of sufentanil that is not contained in the delivery device); (4) the risk of overdosing and resulting toxic reactions are decreased (e.g., risk of overdose due to patient or health professional error during administration is avoided); (5) patient compliance is increased (e.g., the device ensures that drug is continually administered throughout the pre-selected therapeutic period); and (6) safe delivery with a wide range of delivery rates. Drug delivery devices suitable for use in the present invention are described in further detail above. Routes of delivery contemplated by the invention include, but are not necessarily limited to, parenteral routes (e.g., subcutaneous, intravenous, intramuscular, intraspinal, and the like). Subcutaneous delivery is a delivery route of particular interest.

Pain Susceptible to Management According to the Methods of the Invention

In general, administration of fentanyl or a fentanyl congener formulation according to the invention can be used to facilitate management of pain that is associated with any of a wide variety of disorders, conditions, or diseases. Causes of pain may be identifiable or unidentifiable. Where identifiable, the origin of pain may be, for example, of malignant, non-malignant, infectious, non-infectious, or autoimmune origin. Of particular interest is the management of pain associated with disorders, diseases, or conditions that require long-term therapy, e.g., chronic and/or persistent diseases or conditions for which therapy involves treatment over a period of several days (e.g., about 3 days to 10 days), to several weeks (e.g., about 3 or 4 weeks to 6 weeks), to several months or years, up to including the remaining lifetime of the subject. Subjects who are not presently suffering from a disease or condition, but who are susceptible to such may also benefit from prophylactic pain management using the devices and methods of the invention, e.g., prior to traumatic surgery. Pain amenable to therapy according to the invention may involve prolonged episodes of pain alternating with pain-free intervals, or substantially unremitting pain that varies in severity.

In general, pain can be somatogenic, neurogenic, or psychogenic. Somatogenic pain can be muscular or skeletal (i.e., osteoarthritis, lumbosacral back pain, posttraumatic, myofascial), visceral (i.e., chronic pancreatitis, ulcer, irritable bowel), ischemic (i.e., arteriosclerosis obliterans), or related to the progression of cancer (e.g., malignant or non-malignant). Neurogenic pain can be due to posttraumatic and postoperative neuralgia, can be related to neuropathies (i.e., diabetes, toxicity, etc.), and can be related to nerve entrapment, facial neuralgia, perineal neuralgia, postamputation, thalamic, causalgia, and reflex sympathetic dystrophy.

Specific examples of conditions, diseases, disorders, and origins of pain amenable to management according to the present invention include, but are not necessarily limited to, cancer pain (e.g., metastatic or non-metastatic cancer), chronic inflammatory disease pain, neuropathic pain, postoperative pain, iatrogenic pain (e.g., pain following invasive procedures or high dose radiation therapy, e.g., involving scar tissue formation resulting in a debilitating compromise of freedom of motion and substantial chronic pain), complex regional pain syndromes, failed-back pain (chronic back pain), soft tissue pain, joints and bone pain, central pain, injury (e.g., debilitating injuries, e.g., paraplegia, quadriplegia, etc., as well as non-debilitating injury (e.g., to back, neck, spine, joints, legs, arms, hands, feet, etc.)), arthritic pain (e.g., rheumatoid arthritis, osteoarthritis, arthritic symptoms of unknown etiology, etc.), hereditary disease (e.g., sickle cell anemia), infectious disease and resulting syndromes (e.g., Lyme disease, AIDS, etc.), chronic headaches (e.g., migranes), causalgia, hyperesthesia, sympathetic dystrophy, phantom limb syndrome, denervation, and the like. Pain can be associated with any portion(s) of the body, e.g.,the musculoskeletal system, visceral organs, skin, nervous system, etc.

Cancer pain is an example of one broad category of pain that can be alleviated according to the methods of the invention. One of the underlying causes of cancer pain is the severe local stretching of tissues by the neoplastic lesion. For example, as the cancer cells proliferate in an unrestricted manner, the tissues in the local region of cancer cell proliferation are subjected to mechanical stress required to displace tissue and accommodate the increased volume occupied by the tumor mass. When the tumor burden is confined to a small enclosed compartment, such as the marrow of a bone, the resulting pressure can result in severe pain. Another cause of pain can result from the aggressive therapies used to combat the patient's cancer, e.g., radiation therapy, chemotherapy, etc. Such cancer therapies can involve localized or widespread tissue damage, resulting in pain.

Pain associated with any type of malignant or non-malignant cancer is amenable to alleviation according to the invention. Specific examples of cancers that can be associated with pain (due to the nature of the cancer itself or therapy to treat the cancer) include, but are not necessarily limited to lung cancer, bladder cancer, melanoma, bone cancer, multiple myeloma, brain cancer, non-Hodgkins lymphoma, breast cancer, oral cancers, cervical cancer, ovarian cancer, colon cancer, rectal cancer, pancreatic cancer, dysplastic nevi, endocrine cancer, prostate cancer, head and neck cancers, sarcoma, Hodgkins disease, skin cancer, kidney cancer, stomach cancer, leukemia, testicular cancer, liver cancer, uterine cancer, and aplastic anemia. Certain types of neuropathic pain can also be amenable to treatment according to the invention.

Chronic back pain, which is also amenable to management using the methods of the invention, is another broad category of pain that can be alleviated by application of the methods of the invention. Chronic back pain is generally due to one or more of the following six causes: (i) stress on intervertebral facet joints, caused by slippage, arthritis, wedging, or scoliosis; (ii) radiculopathy, the mechanical compression of the nerve root due to bulging discs or tumors; (iii) tendonitis or tendon sprain; (iv) muscle spasm or muscle sprain; (v) ischemia, a local insufficiency in circulatory flow; and (vi) neuropathy, damage to nervous tissue of metabolic etiology or arising from cord tumors or central nervous system disease.

The methods of the invention can be used to manage pain in patients who are opioid naive or who are no longer opioid naive. Exemplary opioid naive patients are those who have not received long-term opioid therapy for pain management. Exemplary non-opioid naive patients are those who have received short-term or long-term opioid therapy and have developed tolerance, dependence, or other undesirable side effect. For example, patients who have intractable adverse side effects with oral, intravenous, or intrathecal morphine, transdermal fentanyl patches, or other conventional methods and devices of opioid delivery can achieve good analgesia and maintain favorable side-effects profiles with delivery of fentanyl or a fentanyl congener when administered in the dose ranges and/or low volume rates described above.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example 1

Formulations Comprising Sufentanil in Benzyl Alcohol 397 mg/mL Formulation 3.97 g of sufentanil base were weighed out and added to a portion of benzyl alcohol. The drug was dissolved in the benzyl alcohol by stirring with a magnetic stirrer. When the resultant preparation was clear, additional benzyl alcohol was added to obtain 10 mL of formulation. The resultant formulation concentration was 397 mg/mL.

310 mg/mL Formulation 3.1 g of sufentanil base were weighed out and added to a portion of benzyl alcohol. The drug was dissolved in the benzyl alcohol by stirring with a magnetic stirrer. When the resultant preparation was clear, additional benzyl alcohol was added to obtain 10 mL of formulation. The resultant formulation concentration was 310 mg/mL.

Example 2

Formulations Comprising Sufentanil in Benzyl Benzoate 248 mg/mL Formulation

The vehicle solution was prepared by adding 3 mL of polysorbate 20 to sufficient benzyl benzoate to make 30 mL of solution. The mixture was stirred using a magnetic stirrer until the polysorbate 20 was dispersed in the benzyl benzoate. 7.44 g sufentanil base was weighed out and added to a portion of the vehicle solution. The drug was dissolved by sonicating the flask in a sonication bath. When the resultant preparation was clear, an additional quantity of the vehicle was added to obtain 30 mL of formulation. The resultant formulation concentration was 248 mg/mL.

77 mg/mL Formulation

The vehicle solution was prepared by adding 3 mL of polysorbate 20 to sufficient benzyl benzoate to make 30 mL of solution. The mixture was stirred using a magnetic stirrer until the polysorbate 20 was dispersed in the benzyl benzoate. 2.322 g sufentanil base was weighed out and added to a portion of the vehicle solution. The drug was dissolved by sonicating the flask in a sonication bath. When the resultant preparation was clear, an additional quantity of the vehicle was added to obtain 30 mL of formulation. The resultant formulation concentration was 77.4 mg/mL.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A pharmaceutical formulation comprising sufentanil in a solution in a non-aqueous diluent, wherein sufentanil is present in the formulation in a concentration from about 50 mg/ml to about 500 mg/ml, and wherein the formulation comprises benzyl alcohol.

2. A method of treating pain in a subject suffering from pain, comprising administering to a subject suffering from pain a formulation according to claim 1, thereby alleviating pain in the subject.

* * * * *